United States Patent
Piletsky et al.

(10) Patent No.: US 6,394,954 B1
(45) Date of Patent: May 28, 2002

(54) METHOD FOR MEASURING THE INTRA-OCULAR PRESSURE THROUGH THE EYELID AND DEVICE FOR REALIZING THE SAME

(75) Inventors: Gennady Konstantinovich Piletsky; Jury Iosifovich Zelenjuk; Konstantin Vasilievich Ivanischev, all of Ryazan; Arkady Pavlovich Nesterov, Moscow; Nikolai Evgenievich Peskov, Ryazan; Nikolai Gennadievich Piletsky, Ryazan; Evgeny Alexeevich Stroev, Ryazan; Alexandr Nikolaevich Chervyakov, Ryazan, all of (RU)

(73) Assignee: Gennady Konstantinovich Piletsky, Ryazan (RU)

( * ) Notice: Subject to any disclaimer, the term of this patent is extended or adjusted under 35 U.S.C. 154(b) by 0 days.

(21) Appl. No.: 09/601,736
(22) PCT Filed: Apr. 30, 1998
(86) PCT No.: PCT/RU98/00140
§ 371 (c)(1),
(2), (4) Date: Aug. 7, 2000
(87) PCT Pub. No.: WO99/39625
PCT Pub. Date: Aug. 12, 1999

(30) Foreign Application Priority Data

Feb. 5, 1998 (RU) ............................................ 98101607

(51) Int. Cl.$^7$ .................................................. A61B 3/16
(52) U.S. Cl. ...................................................... 600/398
(58) Field of Search ................................. 600/398, 399, 600/400, 401, 402, 403, 404, 405, 406

(56) References Cited

U.S. PATENT DOCUMENTS 4,766,904 A * 8/1988 Kozin et al. ................. 600/405
5,197,473 A * 3/1993 Fedorov et al. ............. 600/405
5,836,873 A * 11/1998 Fresco ......................... 600/398

* cited by examiner

Primary Examiner—Kevin Shaver
Assistant Examiner—Pamela Wingood
(74) Attorney, Agent, or Firm—Connolly Bove Lodge & Hutz LLP

(57) ABSTRACT

A method of measuring intraocular pressure through an eyelid includes the step of subjecting the gristle region of an opened eyelid to two spaced contacts providing static support loading that deforms the eyelid. Simultaneously, the gristle region of the eyelid is subjected to the dynamic deformation of a body falling freely relative to the support contacts, such dynamic deformation being transferred to an eyeball area below the eyelid. The spaced contacts are located at equal distances from an axis of displacement of the freely falling body, thereby providing a decrease of eyeball shock absorption under the support. The amount of resilient deformation of a surface of the eyeball is then determined.

19 Claims, 4 Drawing Sheets

METHOD FOR MEASURING THE INTRA-OCULAR PRESSURE THROUGH THE EYELID AND DEVICE FOR REALIZING THE SAME

FIELD OF THE INVENTION

The proposal relates to medicine, and particularly to ophthalmology, and it may be used for measuring intraocular pressure (IOP) through the eyelid both in the cornea region, and in the sclerotic region of an eye by means of express method during mass examination of population on glaucoma, during checking of the correctness of its treatment and during individual control of intraocular pressure without eye anesthetization.

BACKGROUND OF THE INVENTION

A method of measuring intraocular pressure is known, comprising static deformation of an eye by means of the weight of a support with annular supporting part and dynamic deformation of an eye cornea through eyelid by means of a ball freely falling from the height 120–150 mm with the weight 0.3–0.7 g and further determining of the amount of pressure by the first ball rebound (RU 2007951, Cl. A 61 B 3/16, 29.06.90).

In the above method measurement accuracy depends greatly upon individual eyelid structure and features (eyelid thickness, resilience etc.).

The square of interaction of a ball with an eyelid and an eye differs depending on resilient features of patients' eyelids and eyes. The above method does not exclude the influence of differences in shock-absorbing features of eyelids.

Using of an annular support does not eliminate eyelid shock-absorption in places of interacting of the support with an eye through eyelid and does not provide stable reliable interaction of the device with an eye during measurement.

Tonometer-indicator is known for measuring and indication intraocular pressure, comprising a housing, a scale and an eyelid-covered cornea deformation means in the form of a ball, disposed in the housing (in a form of a tube) with transparent working part, enabled to fall free inside the housing and being retained in the upper non-working state by means of a holder, secured in the upper part of the housing, and a stop member, secured in the lower part of the housing for limiting the lower position of the ball (RU 2007951, Cl. A61B 3/16, 29.06.90).

The eyelid deformation by the annular supporting part of the tonometer does not eliminate shock-absorption of an eyelid in the setting place. Besides the rigidity of the connection of the support with an eye is not provided in this tonometer.

A device is known for measuring intraocular pressure, comprising a housing, a bush located within the housing, being adapted to reciprocate within limits and having guides and a supporting part for creating constant set load, an eyelid deformation member, located within a bushing, being adapted to fall in the guides under the influence of its own weight for creating striking load, a holder for retaining the deformation member in the initial upper non-working position, located in the upper part of the bush inside, the lower guide being the stop member for the lower position of the deformation member inside the bush, and the measuring transformer of the linear displacement of the deformation member (RU 2099000, Cl A61B 3/16, 20.12.97).

Using of a falling rod increases the accuracy of measuring IOP because of a small area of its base for eye deformation. However the annular supporting part does not provide the rigidity of the connection of the device with the eyelid-covered eye and does not eliminate shock-absorption of an eyelid.

Thus in all the known devices deformation of an eyelid by the annular supporting portion does not eliminate the influence of the shock-absorption features of an eyelid, which decreases the accuracy of measurement of IOP.

Besides large area of the annular support does not permit to place it on small gristle section of an eyelid.

SUMMARY OF THE PRESENT INVENTION

The technical result at which the proposal is aimed consists in increasing of accuracy of measurement of IOP by means of eliminating the influence of shock-absorption of an eyelid and by means of increasing the rigidity of the connection of the supporting portion with the eye because of static eyelid deformation by the support weight while measuring IOP in the gristle region.

Additionally there is provided stability of maintenance of the distance between the eyelid surface, on which dynamic deformation of an eye is realized, and the rod base in its initial position.

To achieve the technical result there is provided a method of measuring intraocular pressure through the eyelid, comprising static deformation of an eyelid by support loading with simultaneous dynamic deformation of an eyeball through an eyelid by a body freely falling relative to the support with further determining the amount of resilient deformation of the eyeball surface, wherein static deformation of an eyelid by support load is realized in its gristle region by two projections of the support, located at equal distances 7–10 mm from the axis of displacement of the freely falling body, providing a decrease of eyelid shock-absorption under the support.

Advantageously the method includes realizing additional static deformation of the eyelid section, on which dynamic deformation of an eye is realized, by subjecting to applanation of the surface of this section parallel to the base plane of the freely falling body by means of pressing the edges of this eyelid section to the eyeball, providing constant distance between its surface and the base of the freely falling body in its initial position.

Advantageously determining the amount of resilient deformation of the eyeball surface, partially covered by an eyelid, is realized from the parameters of the time function of displacement of a freely falling body.

Preferably in the course of measuring dynamic deformation of an eyeball is realized by means of a flat base with the area 1–7 mm$^2$ of a freely falling body having the form of a rod.

To achieve the technical result there is provided a device for measuring intraocular pressure comprising a housing, a bushing located within the housing, being adapted to reciprocate within limits and having guides and a supporting part for creating constant set load, an eyeball deformation member in the form of a freely falling body, located within the bushing, being adapted to fall freely in the guides under the influence of its own weight for creating striking load, a holder for retaining the eyeball deformation member in the initial upper position, located in the upper part of the bushing inside, the lower guide being the stop member for the lower non-working position of the eyeball deformation member inside the bushing, and a measuring transformer of the linear displacement of the deformation member, the supporting part of the bushing having two projections with rounded supporting ends, located at equal distances 7–10 mm from the axis of displacement of the freely falling body.

Preferably, the projections of the supporting part of the bush are wedge-shaped, and their working surfaces facing each other have the angle of slope equal to 10–30° to the displacement axis of the freely falling body.

Advantageously, facing each confronting working surface of the projections of the supporting part of the bushing has the height 5–10 mm, the width 4–6 mm and the radius of rounded supporting ends 2–3 mm.

Advantageously, confronting working surfaces of the projections of the supporting part of the bushing, have concave form. Preferably, the supporting part of the bushing has a member for applanation of an eyelid section surface, contacting with the freely falling body during striking loading, parallel to the base surface of the later for providing constant distance between the eyelid section surface and the base of the freely falling body in the initial position.

Advantageously, the member for applanation of an eyelid section surface, contacting with the freely falling body during striking loading, has the form of an annular projection 2–3 mm high, which working pressing base is located at the height 3–5 mm from the bases of the projections of the supporting part of the bush.

Advantageously, the supporting part of the bushing has recesses at the butt working surface between the annular and wedge-shaped projections.

Advantageously the supporting part of the bushing has channels for letting air out of the bushing during body falling.

Advantageously, the walls of the bushing outside is supporting part have channels for letting air out, connected with the bushing inside.

Preferably, the deformation member has the form of a rod with a displacement limiting member.

Advantageously, the rod displacement limiting member has the form of a cylinder, rigidly connected with the rod coaxially with it.

Advantageously, the end part of the rod contacting with an eyelid during striking loading has the length not less than 3 mm and a flat base with the area 1–7 mm$^2$.

Advantageously, the rod holder has the form of a horizontal spring plate catch with a hole for catching the upper end of the rod and with a splay on a side surface for interaction with a pin, secured on the wall of the housing, the upper end of the rod has a stop member for interaction with the plate catch, and the pin serves as a drive of horizontal displacement of the plate catch while displacing the housing downward relative to the bushing.

Preferably, the measuring transformer of the linear displacement of the eyeball deformation member comprises a generator connected with an electromagnetic coil, secured in the bushing between the guides, and a data processing device, and the rod displacement limiting means serves as the core of the electromagnetic coil.

Advantageously, the device includes a means for fixing the bushing in the initial position in the housing, including sprung button, pressing part of which is located in a hole of the housing wall enabled to interact with the outer surface of the bushing.

Using of the supporting portion with projections with small base area permits the increase of loading of the support on the eyelid in their setting places, providing pressing of the eyelid to eliminate its shock-absorption, and to provide rigid connection of the supporting portion of the device with the eye during measurement.

Besides placing the support projections on the eyelid in the gristle region eliminates eye deformation under the projections.

The proposal is illustrated by the following drawings.

DESCRIPTION OF PREFERRED EMBODIMENTS

Figure 1:
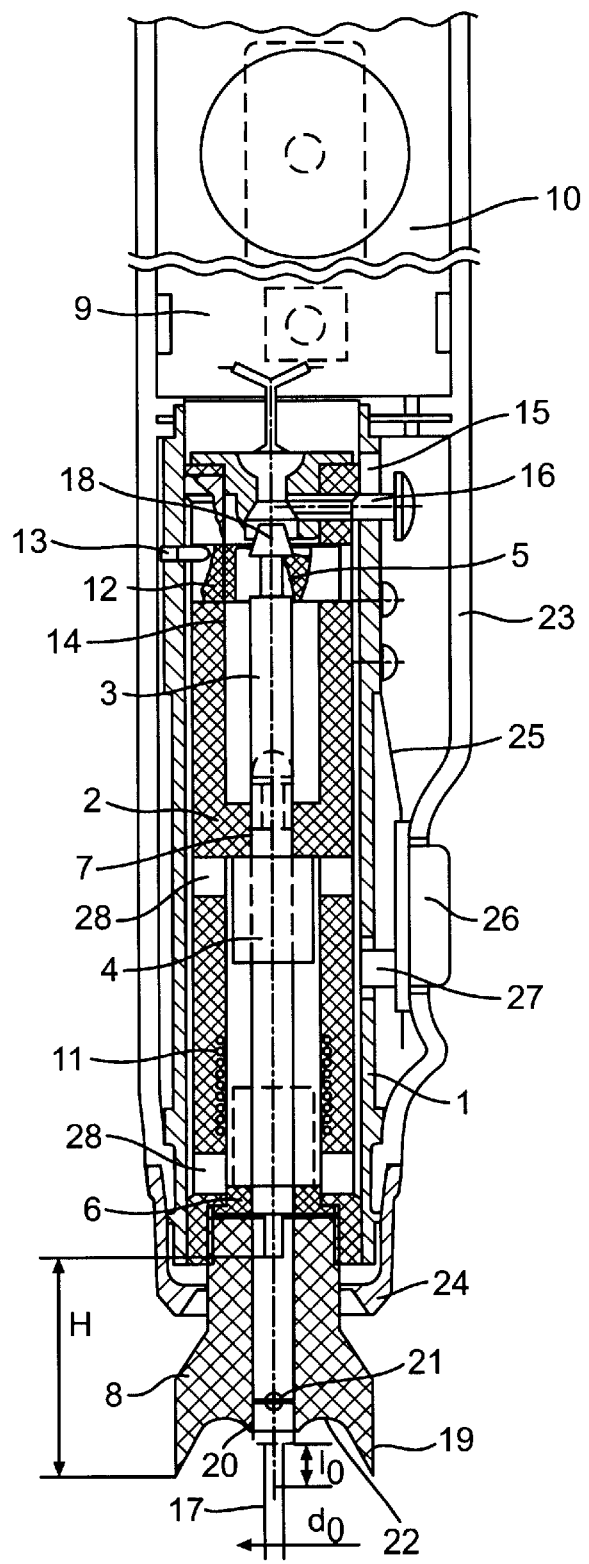
FIG. 1 is a general view of a device for measuring intraocular pressure.
Figure 3:
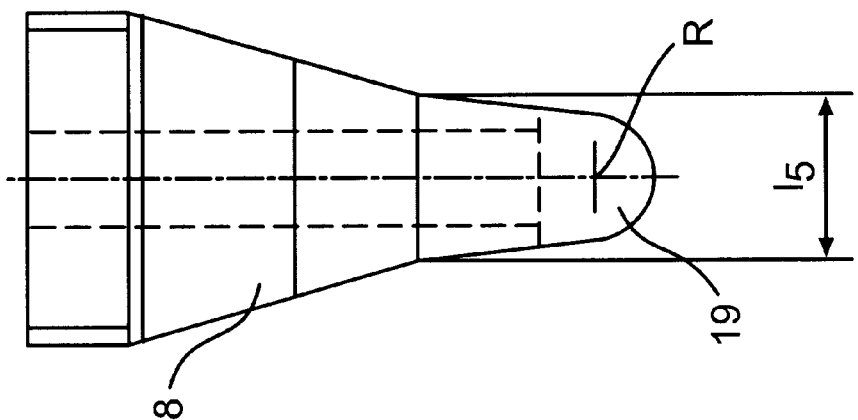
FIG. 3 is a side view of FIG. 2, showing the form of the projections on the supporting part of a bushing.
Figure 2:
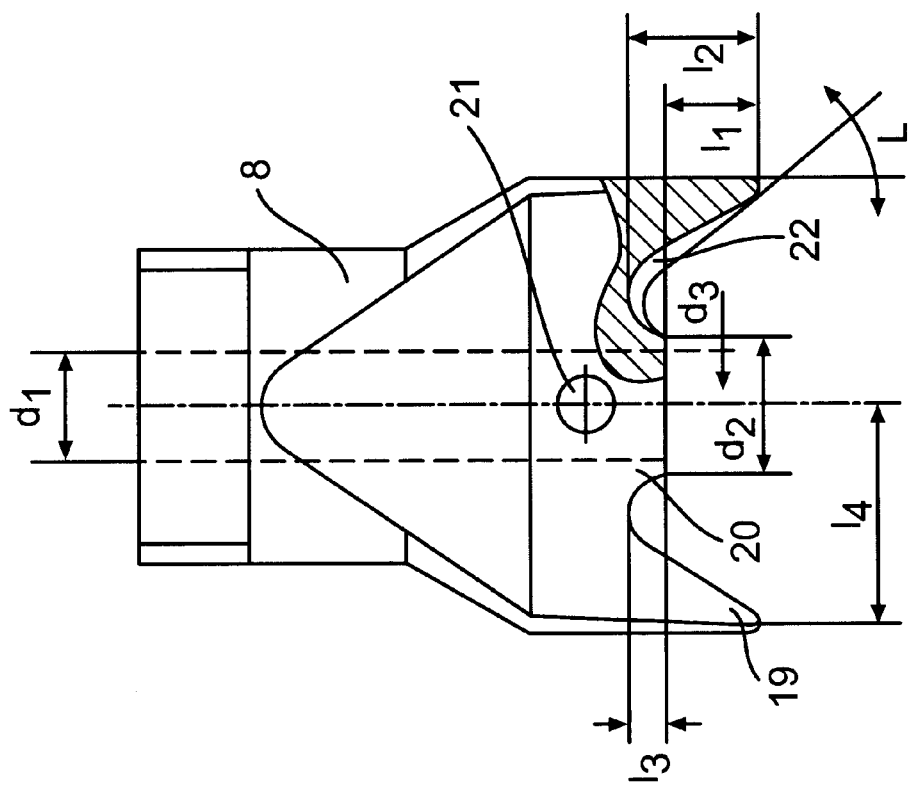
FIG. 2 is a partial view of the supporting portion of a bushing.
Figure 4:
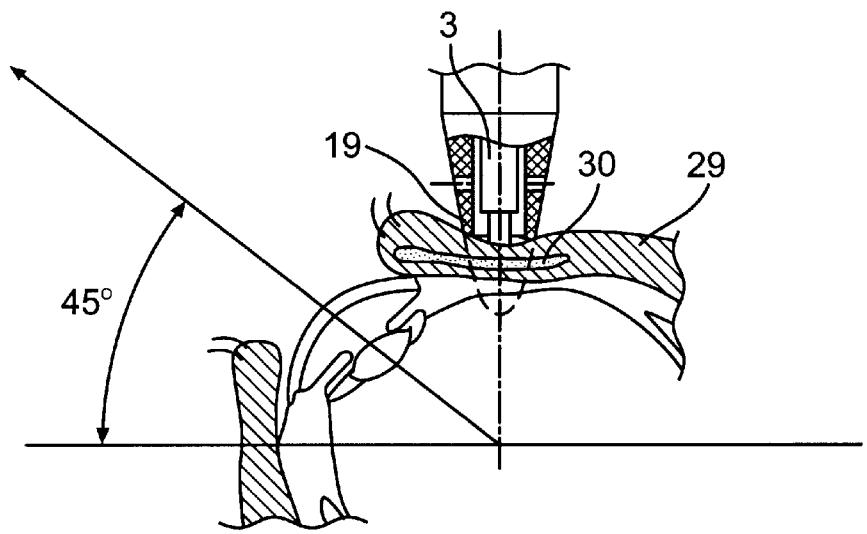
FIG. 4 shows an example of placing of the device on a gristle region.
Figure 5:
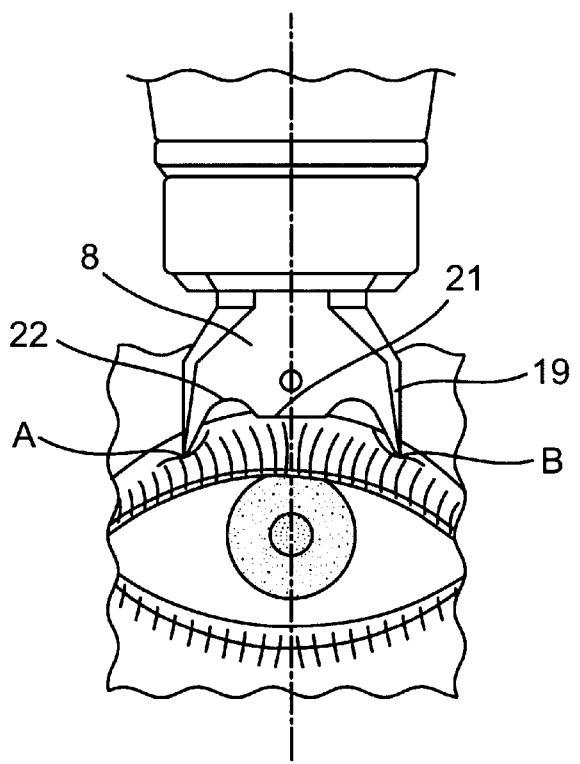
FIG. 5 shows placing of the device for providing rigid connection of the support with an eye.
Figure 6:
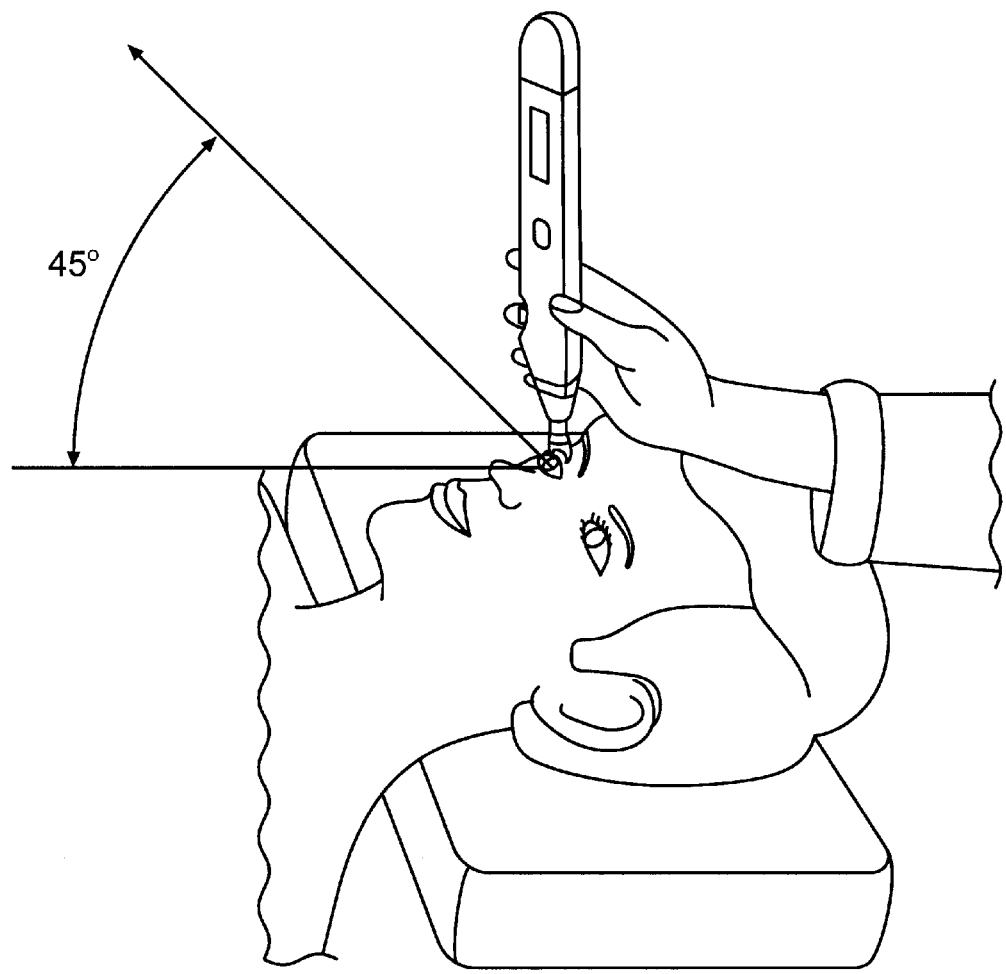
FIG. 6 shows placing of the device while working with a patient.

Measuring intraocular pressure with the help of the proposed device is carried out in following manner: the device is placed on the patient's eyelid in vertical position (FIG. 6), acting upon an eye through an eyelid in its gristle region (FIG. 4) by two wedge-shaped projections set in two points (A and B), located at equal distances 7–10 mm from the displacement axis of the falling body parallel with the horizontal eye meridian and symmetrically from the axis, passing through the eye center (FIG. 5) for providing rigid connection of the device support with an eye.

Acting upon an eyelid-covered eye by the support projections with small base area in the gristle region eliminates eyelid shock-absorption. During measuring IOP (FIG. 6) dynamic deformation of an eyelid and an eyeball (in a sclera or cornea region depending upon preliminary set patient's visual angle) realized with a freely falling body in the form of a rod, by time function of which displacement they judge about IOP.

A device for measuring intraocular pressure comprises a housing 1 and a bushing 2, located in the housing 1, being adapted to reciprocate vertically within limits (without rotary movement) for creating constant load. An eye deformation member has the form of a rod 3 with a displacement limiting member 4. A holder 5 for retaining the eyeball deformation member in the initial position is located in the upper part of the bushing. A first guide 6 for the rod 3 has the form of a washer, installed in the bushing walls. A second guide 7 for the rod 3 is made in the bushing 2. A supporting part 8 of the bushing 2 is secured at the lower part of the bush 2, for example, by means of a threading.

A measuring transformer has the form of a generator 9, a data processing device 10 and connected with the generator 9 electromagnetic coil 11, secured in the bushing 2 between the guides 6, 7. The rod displacement limiting means 4 is made from ferric material or brass, is located inside the bushing 2 in the initial position higher than the coil 11 and serves as its core. It is possible to use other materials for the means 4 providing changing of the coil 11 inductance during falling of the rod 3.

The rod 3 is installed in the holes of the guides 6, 7 with a lash 0.05–0.1 mm, enabling the rod 3 falling under the influence of its own weight inside the bushing 2 while orienting the device along the vertical axis in one direction (working position, when the supporting part 8 of the bushing 2 is below, and the rod is fixed in the holder 5 in the initial position) and in another direction (while returning the rod 3 after measuring to the initial position).

The holder 5 of the rod 3 in the initial position has the form of a plate catch with a hole (conical) for catching the upper end of the rod 3 and with a splay 12 on a side surface. A pin 13, secured in the housing 1, serves as a drive of horizontal displacement of the spring plate catch 5 during vertical displacement of the pin 13 down along the splay surface in the course of moving the housing 1 downward.

The upper end of the rod 3 is made with a stop member 18 for reliable fixing of the rod 3 in the hole of the plate catch 5.

The supporting part 8 of the bush 2 is made with two wedge-shaped projections 19 with rounded supporting ends, located at equal distances $l_4=7-10$ mm from the displacement axis of the rod 3.

Preferably the projections 19 on the supporting part 8 of the bush 2 are wedge-shaped, and their working surfaces, facing each other, in particular, have concave form, have angle of slope 10–30° to the displacement axis of the freely falling body, have the height $l_2=5-10$ mm, the width $l_5=4-6$ mm and the radius of rounded supporting ends R=2–3 mm.

The projections 19 are to create the basic static load at the points of their placing on the eyelid and they have the form, enabling the basic summary load on the eyelid from the support being enough for eliminating self-absorption of an eyelid at the base of the projections 19.

Load (P) of the support, acting upon an eyeball, in the initial position of the rod 3, consists of the weights of the moving bushing 2 with the supporting part 8 and the rod 3 with the member 4.

This load (P, g), the width of the projections 19 ($l_5$, mm) and the radius of the rounded supporting ends (R, mm) correlate as follows:

$$\frac{P}{l_5 * R} = 1.4 - 3.0$$

The lower value of the correlation is limited by degree of eliminating self-absorption of the eyelid at the bases of the projections 19 on the supporting part 8, and the higher value is limited by the influence of the load upon eye deformation: a large value of eye deformation decreases the accuracy of measuring IOP.

The supporting part 8 of the bushing 2 may have a member for applanation of an eyelid section surface, contacting with the freely falling body 3 during striking loading, to make it parallel to the base surface of the later for providing constant distance between the eyelid section surface and the base of the freely falling body 3 in the initial position.

The member for application of an eyelid section may have the form of annular projection 20 with the width d=0.5–1 mm, the height $l_2=2-3$ mm. Working pressing base of this member is located at the height $l_1=3-5$ mm from the bases of the projections 19 on the supporting part of the bushing 2. Besides the outer diameter ($d_2$) of the annular projection 20 exceeds the diameter ($d_1$) of the inside of the supporting part 8.

The member 20 limits and subjects to application the eyelid section area, at which the eye deformation takes place by means of the rod 3, but the member 20 does not deform the eye. This provides stability of maintaining a fixed (set) distance in the initial position between the plane surface of the end part 17 of the rod 3 and the eyelid surface for different anatomic structures of an eye and an eyelid. This is being done in order to flatten an eyelid and eliminate the eye deformation under the annular projection 20.

For letting air out the bushing during body falling the supporting part 8 of the bushing 2 may have channels 21 (in the form of through decompressing holes), connected with the inside of the bushing 2.

For concentrating of the larger part of the support weight (the bushing 2 with the support part 8 and the rod 3) on the eyelid under the projections 19 during measuring the supporting part 8 of the bushing 2 has recesses 22 at the surface between the projections 19 and the member 20. And the said surface of the supporting part 8 of the bushing 2 on the whole is made concave.

The housing 1 may be placed in a protective (removable) casing 23, rigidly joined with the housing 1 by a decorative bushing 24. Besides the protective casing 23 and the housing 1 are mounted to enable their joint reciprocating relatively to the bushing 2 placed on the eye in the limits of displacing of the pin 16 in the aperture 15.

Additionally the device is supplied with a means for fixing (clamping) the bushing 2 in the initial position in the housing 1. The means for fixing may have the form of a button 26, biased by the plate 25. The braking part 27 of the button 26 is placed in a hole in the wall of the housing 1 to interact with the outer surface of the bush 2. Pressing of the button 26 provides retaining of the bushing 2 in the lower position while placing the rod 3 in the initial position by means of overturning of the protective casing 23 (and of the housing 1) with the supporting part 8 upward and while placing the device on a patient's eyelid.

Advantageously the walls of the bushing 2 have channels 28 (in the form of apertures) for letting air out during displacement of the rod 3.

The device functions as follows. A patient's head is placed with his face up. The direction of his line of sight is set approximately at the angle 45° to the horizon for eye deformation in the gristle region (or 90° for eye deformation of the cornea center through an eyelid by the rod 3) using, for example, a patient's hand as a guiding line.

While holding the device for measuring IOP by its casing 23, with the button 26 pressed for disenable untimely movement of the rod 3 out of the initial position, the supporting part 8 of the movable bush 2 is placed on the section of an upper eyelid 29 by the projections 19 in the region of its gristle 30 (FIG. 4) symmetrically to the eyeball center. The axis of the movable bushing 2 is to be vertical and passes through the eyeball center.

Besides the additional annular projection 20 subjects the eyelid to application at the spot of its meeting with the base of the falling rod 3. It is necessary to equalize the height of the free falling of the rod 3 for different anatomical structures of an eye and an eyelid.

Then after setting free the button 26 the protecting casing 23 is moved downward. And the plate catch 5 displaces horizontally inside the movable bush 2, sets the stop member 18 free and the rod 3 falls free in the guides 6 and 7 on the examined eye of the patient. During the movement of the casing 23 the rod 3 is set free when the pin 16 is situated in the middle of aperture 15, which is provided by static loading on the eyelid with the device. In this condition the pressure of the casing 23 and the housing 1 on the eye is excluded. Displacing of the plate catch 5 happens owing to the changing position of the pin 13 during downward movement of the protective casing 23. While falling, the rod 3 deforms an eyelid and an eye with its base, then it rebounds backward.

Figure 7:
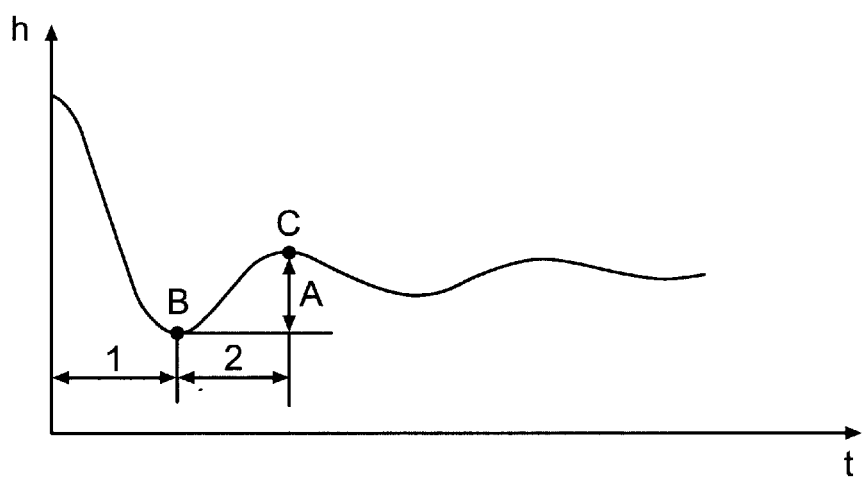
FIG. 7 is a graphic time function of the rod displacement.

The member 4, situated on the rod 3, while moving down (during falling of the rod 3) and up (during rebounding of the rod 3) causes changing of inductance of the electromagnetic coil 11, leading to changing of frequency of the generator 9. This frequency change is fixed in the course of time by the data processing device 10 and transforms to the value of displacement of the rod 3 relative to the moving bushing 2. The received time function of the rod displacement is shown at the FIG. 7: the part 1 corresponds to the free falling of the rod 3 and its interaction with an eye through an eyelid and a gristle during its forward movement, and the part 2—during its rebound. The amount of IOP may be determined, for example, from the amplitude A of the first rebound or from accelerations relative to point B, corresponding to maximum eye deformation and be determined as the first minimum of the function of displacement. Or the amount of IOP may be determined with another known method of function processing.

Preparation of the device for the next measurement is fulfilled as follows. While holding the device by the casing 23 with the supporting part 8 downward, the button 26 is pressed and the device is overturned with the supporting part 8 upward. The rod 3, moving under the influence of its own weight, comes into engagement by its stop member 18 with the plane catch 5 and is fixed.

Then the device is returned to unitial position (with the supporting part 8 downward).

INDUSTRIAL APPLICABILITY

The applied device provides measurement of intraocular pressure in mm Hg with accuracy ±0.6 mm Hg. The measurement time is not more than 3 sec.

The procedure is painless, does not require anesthetization of an eye and enables measuring of IOP for children of any age, which is very important in connection with increasing of number of cases of glaucoma not only among the adult population, but among children.

Possibility of deformation while measuring in the sclera region not only simplifies the process of measuring IOP, by essentially widens the possibility of using the applied method and device, for instance, in case of cornea pathology or through keratoplastics.

The applied methods and device exclude the risk of bringing infection during measurement owing to absence of direct contact with the mucous membrane of an eye.

The applied method and device enable to fulfil multiple measurements of IOP on the same patient during twenty-four hours, which is very important for checking of the correctness of the chosen method of glaucoma treatment and enables to increase essentially its effectiveness.

The simplicity of the applied construction enables its manufacture at an accessible price, and the simplicity of usage applies not only in clinical conditions, but in domestic ones.

The proposed technical decision increases accuracy of measurement of IOP owing to decreasing shock-absorption of an eyelid and enables watching IOP changes in the course of treatment. Below the comparative table is given, showing the advantages of the applied device relative known ones.

TABLE 1

| Index 1 | The proposed device (tonometer) 2 | The home analogue-tonometer-tonograph digital TND - 100° C. 3 | Foreign analogue-tonometer TONOPEN (USA) 4 |
| --- | --- | --- | --- |
| 1. Measurement range (mm Hg) | 5–80 | 4–60 | 5–80 |
| 2. Accessible measurement error, % | 3 | 2 | 9 |
| 3. Measurement time, S | 3 | 120 | 5 |
| 4. Possibility of usage in domestic conditions | yes | no | no |
| 5. Necessity of anesthetization | not required | required | required |
| 6. Necessity of sterilization or one occasion sterile cap | Not required | required | required one occasion sterile cap |
| 7. Mass, g | 75 | 5500 | 64 |
| 8. Dimensions, mm | 173.5 ×25.5 ×19.5 | 310 ×190 ×260 | 174 ×24 ×21 |

What is claimed is:

1. A device for measuring intraocular pressure, comprising a housing; a bushing located within the housing being adapted to reciprocate within limits and having guides and a supporting part for creating a constant set load; an eyeball deformation member in the form of freely falling body, located within the bushing, being adapted to fall freely in the guides under the influence of its own weight for creating a striking load; a holder for retaining the eyeball deformation member in the initial upper position, located in the upper part of the bushing inside; the lower guide being a stop member for a lower non-working position of said deformation member inside the bushing; and a measuring transformer of the linear displacement of said deformation member; the supporting part of the bushing being made with two projections having rounded supporting ends, located at equal distances from an axis of displacement of the freely falling body.

2. A device as claimed in claim 1, wherein the projections of the supporting part of the bushing are wedge-shaped, and their confronting working surfaces have an angle of slope 10–30° to the axis of displacement of the freely falling body.

3. A device as claimed in claim 1, each of the working surfaces of the projections of the supporting part of the bushing has the height 4–6 mm, the width 4–6 mm and the radius of rounded supporting ends 2–3 mm.

4. A device as claimed in claim 1, wherein each working surface of the projections of the supporting part of the bushing has a concave form.

5. A device as claimed in claim 1, the supporting part of the bushing has a member for application of an eyelid section surface, contacting with the freely falling body during striking loading, parallel to the base surface of the later for providing constant distance between the eyelid section surface and the base of the freely falling body in the initial position.

6. A device as claimed in claim 5, wherein the member for applanation of an eyelid section surface, contacting with a freely falling body during striking loading, has the form of an annular projection 2–3 mm high, which working pressing base is located at the height 3–5 mm from the bases of the projections of the supporting part of the bushing.

7. A device as claimed in claim 1, wherein the supporting part of the bushing has recesses at the butt working surface between the annular and wedge-shaped projections.

8. A device as claimed in claim 1, the supporting part of the bushing has channels for letting air out of the bushing during falling of the body.

9. A device as claimed in claim 1, wherein the walls of the bushing outside its supporting part have channels for letting air out, connected with the bushing inside.

10. A device as claimed in claim 1, wherein the deformation member has the form of a rod with a displacement limiting member.

11. A device as claimed in claim 10, wherein the rod displacement limiting member has the form of a cylinder, rigidly connected with the rod coaxially with it.

12. A device as claimed in claim 11, wherein the end part of the rod, contacting an eyelid during striking loading, has a length of not less than 3 mm and a flat base with the area 1–7 mm.

13. A device claimed as in claim 10, wherein the rod holder has the form of a horizontal spring plate catch with a hole for catching the upper end of the rod and with a splay on a side surface for interaction with a pin, secured on the wall of the housing, the upper end of the rod has a stop member for interaction with the plate catch and the pin serves as a drive of horizontal displacement of the plate catch while displacing the housing downward relative to the bushing.

14. A device as claimed in claim 10, wherein the measuring transformer of the linear displacement of the eyeball deformation member comprises a generator, connected with an electromagnetic coil, secured in the bushing between the guides, and a data processing device, and the rod displacing limiting means serves as the core of the electromagnetic coil.

15. A device claimed as in claim 1, wherein the device includes a means for fixing the bushing in the initial position in the housing, having the form of a spring button, a pressing part of which is located in a hole of the housing wall enabled to interact with the outer surface of the bushing.

16. A method of measuring intraocular pressure through the eyelid of an open eye comprising the steps:

subjecting the gristle region of an opened eyelid to two spaced contacts providing static support loading that deforms the eyelid;

simultaneously subjecting the gristle region of the eyelid to dynamic deformation of a body falling freely relative to the support contacts, such dynamic deformation being transferred to an eyeball area below the eyelid;

the spaced contacts being located at equal distances 7–10 mm from an axis of displacement of the freely falling body, thereby providing a decrease of eyeball shock absorption under the support; and determining the amount of resilient deformation of a surface of the eyeball.

17. The method of claim 16 together with the additional step of pressing edges of the gristle region of the eyelid against the eyeball to achieve applanation of this region parallel to a base plane of the freely falling body thereby providing constant distance between the gristle region of the eyelid and the base of the freely falling body.

18. The method of claim 16 wherein the amount of resilient deformation of the eyeball surface is determined from parameters of a time function of displacement of the freely falling body.

19. The method as claimed in claim 16 wherein, during the dynamic deformation, the eyelid is subjected to a flat outer base of a rod, the rod being the falling body.

\* \* \* \* \*